(12) United States Patent
Menin et al.

(10) Patent No.: US 11,937,620 B2
(45) Date of Patent: Mar. 26, 2024

(54) YEAST PROTEINS

(71) Applicant: LESAFFRE ET COMPAGNIE, Paris (FR)

(72) Inventors: Rudy Menin, Choisy le Roi (FR); Pauline Spolaore, Sucy-en-Brie (FR); Isabelle Mouly, Marcq-en-Baroeul (FR)

(73) Assignee: LESAFFRE ET COMPAGNIE, Paris (FR)

( * ) Notice: Subject to any disclaimer, the term of this patent is extended or adjusted under 35 U.S.C. 154(b) by 0 days.

(21) Appl. No.: 18/153,797

(22) Filed: Jan. 12, 2023

(65) Prior Publication Data
US 2023/0165271 A1 Jun. 1, 2023

Related U.S. Application Data

(62) Division of application No. 17/049,897, filed as application No. PCT/EP2019/060750 on Apr. 26, 2019, now Pat. No. 11,602,156.

(30) Foreign Application Priority Data

Apr. 27, 2018 (FR) ...................... 1853748

(51) Int. Cl.
*A23J 1/18* (2006.01)
*A23L 31/10* (2016.01)
(Continued)

(52) U.S. Cl.
CPC ................. *A23J 1/18* (2013.01); *A23L 31/10* (2016.08); *A23L 33/14* (2016.08); *C12N 1/063* (2013.01)

(58) Field of Classification Search
CPC .. A23J 1/18; A23L 31/10; A23L 33/14; C12N 1/063
See application file for complete search history.

(56) References Cited

U.S. PATENT DOCUMENTS 3,867,555 A 2/1975 Newell et al.
3,887,431 A 6/1975 Robbins et al.
(Continued)

FOREIGN PATENT DOCUMENTS

DE 850286 C 9/1952
FR 2207985 A1 6/1974
(Continued)

OTHER PUBLICATIONS

Notice of Allowance for U.S. Appl. No. 17/049,897, entitled "Yeast Proteins" dated Oct. 26, 2022.
(Continued)

*Primary Examiner* — Donald R Spamer
*Assistant Examiner* — Jeffrey D Benson
(74) *Attorney, Agent, or Firm* — Hamilton, Brook, Smith & Reynolds, P.C.

(57) ABSTRACT

The present invention relates to a method for obtaining yeast proteins comprising the following steps: a) providing a yeast cream; b) exposing this yeast cream to a thermal plasmolysis at a temperature between 70 and 95° C. for a time of between 30 seconds and 4 hours; c) subjecting the whole to the activity of at least one ribonuclease and a glucanase, sequentially or simultaneously, at a temperature between 40 and 65° C. for a period of between 8 and 24 hours; and d) separating the insoluble fraction from the soluble fraction; wherein the insoluble fraction collected in step d) is taste-free, has a nucleotide content less than 3% and a true protein content of at least 72%.

10 Claims, 2 Drawing Sheets

(51) Int. Cl.
*A23L 33/14* (2016.01)
*C12N 1/06* (2006.01)

(56) References Cited

U.S. PATENT DOCUMENTS

| | | | |
|---|---|---|---|
| 3,991,215 | A | 11/1976 | Robbins |
| 4,080,260 | A | 3/1978 | Chao |
| 9,115,379 | B2 * | 8/2015 | Noordam ............... A23L 33/145 |
| 11,602,156 | B2 | 3/2023 | Menin et al. |
| 2009/0123990 | A1 | 5/2009 | Bergmaier |
| 2009/0324778 | A1 * | 12/2009 | Oriol ........................ C12P 19/30 |
| | | | 426/62 |
| 2011/0052514 | A1 * | 3/2011 | Justen .................... A61Q 19/08 |
| | | | 424/59 |
| 2021/0267230 | A1 | 9/2021 | Menin et al. |

FOREIGN PATENT DOCUMENTS

| | | |
|---|---|---|
| FR | 3074811 | 6/2019 |
| GB | 554010 A | 6/1943 |
| JP | 52-130992 A | 11/1977 |
| JP | 2009-137916 A | 6/2009 |
| JP | 2013-053083 A | 3/2013 |
| SU | 1034688 A | 8/1983 |
| WO | 03078605 A1 | 9/2003 |
| WO | 2010/096382 A1 | 8/2010 |

OTHER PUBLICATIONS

Notice of Allowability for U.S. Appl. No. 17/049,897, entitled "Yeast Proteins" dated Jan. 24, 2023.
Japanese Office Action and Search Report with English Translations Japanese Patent Application No. 2020-560212 dated Dec. 13, 2022.
Reed, et al., "Yeast Technology," pp. 284-293, an Avi Book published by Van Nostrand Reinhold, NY (ISBN 0-442-31892-8), copyright 1991.
PCT International Search Report and Written Opinion for International Application No. PCT/EP2019/060750, entitled "Yeast Proteins," dated May 17, 2019.
Russian Office Action and Search Report with English Translations from the Federal Service on Intellectual Property, Application No. 2020138243, dated Aug. 4, 2022.
Chinese Office Action and Search Report with English Translations, Chinese Patent Application No. 201980028345.9 dated Dec. 28, 2022.
Tong, "Nutrition and Application of Yeast Proteins", Food Science, vol. 10, No. 4, Dec. 31, 1989, pp. 12-15.

* cited by examiner

YEAST PROTEINS

RELATED APPLICATIONS

This application is a divisional of U.S. application Ser. No. 17/049,897, filed Oct. 22, 2020, which is the U.S. National Stage of International Application No. PCT/EP2019/060750, filed on Apr. 26, 2019, which designates the U.S., published in French, and claims priority under 35 U.S.C. § 119 or 365(c) to France Application No. 1853748, filed on Apr. 27, 2018. The entire teachings of the above applications are incorporated herein by reference.

BACKGROUND

The present invention relates to the field of proteins derived from microorganisms, and more specifically derived from yeasts, that can be widely used for human and animal nutrition, health and well-being.

BIBLIOGRAPHY

Proteins represent the chief component of human and animal tissue. From a nutritional viewpoint, proteins are hydrolysed by proteases and peptidases into peptides and amino acids. Amino acids provide essential elements for the body such as nitrogen, carbohydrates and sulphur. The body does not fix mineral nitrogen for incorporation thereof in organic molecules: nitrogen is therefore provided by amino acids. Sulphur-containing amino acids provide sulphur of importance for metabolism. Amino acids are also essential elements for the synthesis of proteins, peptides and substances of low molecular weight that are physiologically essential such as glutathione, creatine, dopamine, serotonin etc. Protein needs for human and animal nutrition are consequently expanding with the increase in world population. There is therefore a need to find additional and/or alternative sources of proteins to animal proteins. Proteins have already been recovered from plants (cereals, legumes) or insects. Obtaining proteins of microbial origin relies on fermenting mechanisms that have been known for centuries. Microbial proteins are either components of the whole cell or cell wall, or isolated proteins. One of the disadvantages of proteins of microbial origin for human food is the nucleic acid content of isolates. This content must be low because one of the end products of the metabolism of nucleic acids is uric acid which the human body, lacking the enzyme uricase required for catabolism thereof, is unable to degrade. Other disadvantages are for example the extraction yield or the purity of proteins obtained via isolation from microorganisms.

After cell lysis e.g. of yeast cells, proteins are conventionally recovered in the «noble» phase i.e. the soluble phase, which corresponds to yeast extracts and contains compounds high in taste. However, taste may be a disadvantage depending on the intended application of the protein extract obtained.

Three patents by one same team concern the obtaining of concentrated protein extracts.

U.S. Pat. No. 3,867,555 discloses a method allowing protein extracts to be obtained having a low content of nucleic acids. The cells are mechanically ruptured (high pressure, ultrasound) or chemically ruptured (autolysis, external enzymes) so that the proteins remain within the soluble fraction. However, these proteins are mixed with the result of hydrolysis i.e. with amino acids, peptides and polysaccharides or simple sugars. After centrifugation to separate and remove the insoluble fraction, the proteins are precipitated and alkaline treatment allows hydrolysis of the nucleic acids which are subsequently removed via filtration. However, the overall recovery yield of «non hydrolysed» proteins is low.

U.S. Pat. No. 3,887,431 discloses the use of the endogenous nuclease found in the soluble fraction after lysis of yeasts, to degrade nucleic acids. A vacuum concentration step allows the obtaining of both a concentrated protein extract and a product having little taste and odour.

U.S. Pat. No. 3,991,215 discloses a method which, after cell rupture, applies ultra-high temperature heat to the soluble cytoplasmic fraction which allows a protein-rich extract to be obtained with few nucleic acids.

Finally, several directions can be followed to improve methods for isolating proteins from microorganisms, with a view to obtaining better purity, better yield and/or protein extracts that can be used directly for nutrition or as food supplements.

SUMMARY OF THE INVENTION

Contrary to the direction taken by usual techniques, the inventors have developed a method for isolating microorganism proteins from the insoluble fraction obtained after lysis of said microorganisms. This novel method allows concentrated extracts of non-hydrolysed proteins to be obtained having scarce nucleic acid content, odour and smell, and with a good yield.

The method of the invention starts with cell lysis, preferably via thermal plasmolysis which leads to inactivation of microorganism enzymes and release into the medium of free amino acids including glutamic acid. These are subjected to an enzyme of glucanase type and an enzyme of ribonuclease type, followed by separation after which the insoluble fraction represents the product of interest having a content of true proteins of at least 72%. In another embodiment of the invention, a first separation is conducted after the thermal plasmolysis phase, and only the insoluble fraction comprising the proteins, polysaccharides and RNA is subjected to the action of a glucanase and ribonuclease and then again separated to maintain the protein-rich insoluble fraction.

The protein extract obtained is free of taste and odour and low in nucleic acids.

The protein extract still containing lipids derived from the membrane can be delipidated with methods known to persons skilled in the art, such as extraction with a solvent of hexane or ethanol type, with supercritical $CO_2$ or via treatment with lipases or phospholipases followed by separation from the solubilised phase.

The proteins obtained can be used directly for applications in nutrition, food supplements, etc.

Definitions

By microorganism is meant a living organism invisible to the naked eye but visible under a microscope. In the present invention, the microorganisms are preferably bacteria (prokaryote microorganisms) or yeast (eukaryote microorganisms). Yeast, in the singular or plural, is a generic term designating eukaryote microorganisms able to cause fermentation of organic matter. Among yeasts, non-exhaustive mention is made of the genii *Saccharomyces, Candida, Pichia, Kluyveromyces*.

Yeast cream designates the suspension of yeasts obtained after multiplication in a vessel and after centrifugation allowing separation of said suspension from the surrounding liquid also called must. Multiplication can also be called culture or, by extension, fermentation.

Proteins are macromolecules formed of a sequence of amino acids linked together via peptide bonds. They figure among the main basic constituents of all animal and plant cells. They represent up to 50 dry weight % of a living being and account for 15 to 20% of our daily energy intake. Food and body proteins are the main sources of nitrogen and amino acids which have several major metabolic functions: they are substrates of protein synthesis, precursors of important nitrogen-containing compounds in the body (nucleic acids, nitrogen monoxide, glutathione, etc.) and substrates of energy metabolism.

In general, in agri-foods, the protein content is considered to be the nitrogen level multiplied by 6.25 (the coefficient 6.25 derives from the average nitrogen content of a protein which is 100/6.25 i.e. 16%). By true proteins, it is meant a protein content closer to reality corrected for bias induced by non-proteinic nitrogen e.g. the nitrogen of nucleic acids. Therefore, as a formula, the content of true proteins can be said to be total nitrogen less the nitrogen from nucleic acids and ammoniacal nitrogen, multiplied by 6.25. Alternatively, the content of true proteins can be evaluated by assay of total amino acids. By intact native proteins, it is meant the proteins of the microorganism in the state in which they are found in the living microorganism. By extension, denatured native proteins have a potentially modified spatial conformation via folding or coagulation. Proteins can also be partly or fully hydrolysed.

By plasmolysis is meant a rupture of the imperviousness of a microorganism, preferably yeast, or of its compartmental aspect. There is loss of water further to permeabilization of the membrane.

BRIEF DESCRIPTION OF THE DRAWINGS

FIG. 1A illustrates the method wherein there is no separation step between plasmolysis and enzymatic hydrolysis. FIG. 1B illustrates the method wherein separation is performed after the plasmolysis step and wherein enzymatic hydrolysis is conducted on the insoluble fraction derived from this separation.

DETAILED DESCRIPTION OF THE INVENTION AND EMBODIMENTS

Figure 1:
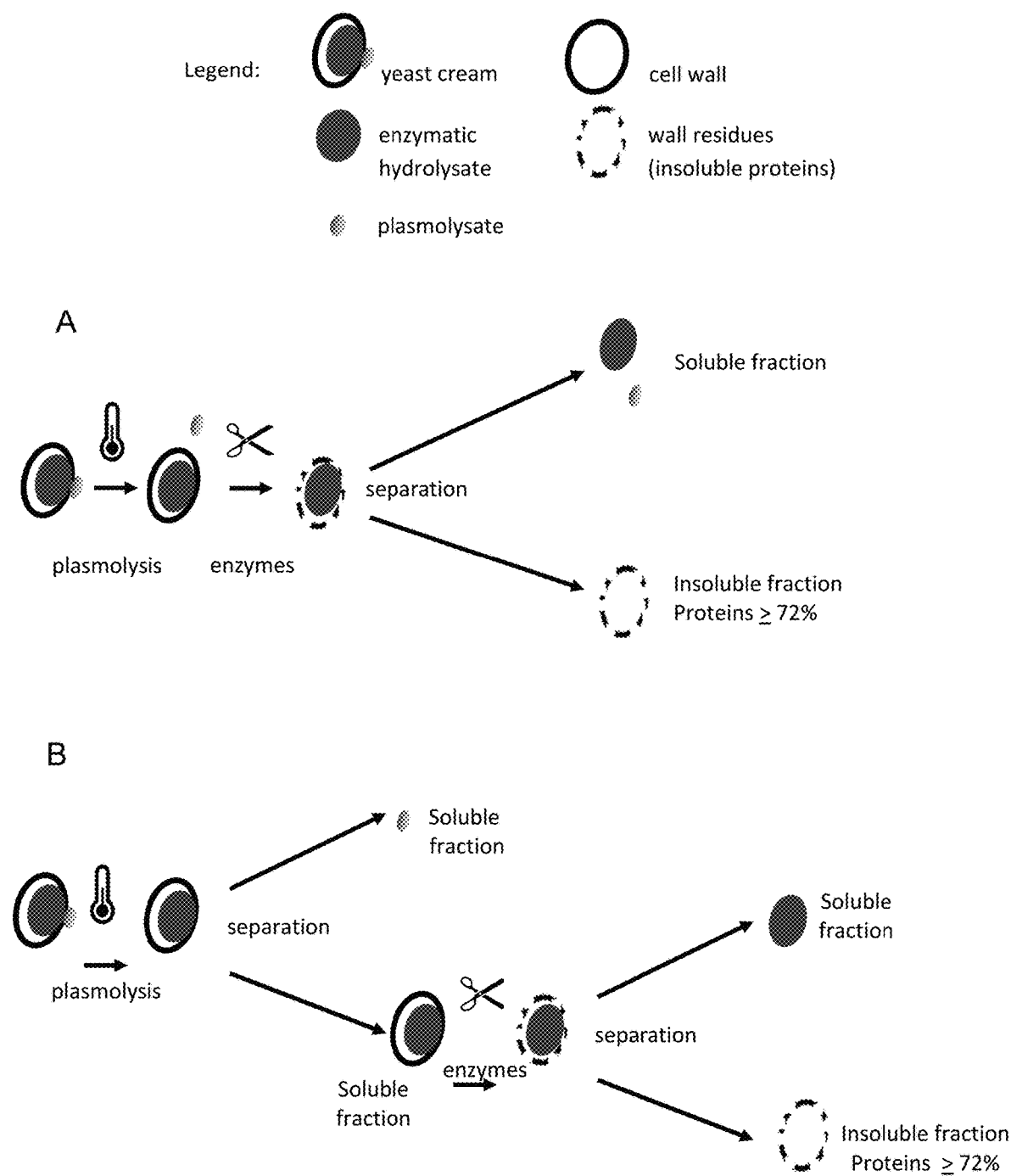
FIG. 1 illustrates the two main embodiments of the method of the invention.

The method of the invention can be applied to any type of yeast, more specifically any yeast having background use in human or animal nutrition. From an industrial viewpoint, the method of the invention is implemented on a yeast cream such as defined in the foregoing, i.e. on a suspension of yeasts. Preferably, the yeasts are selected from among the yeasts of genii *Saccharomyces, Pichia, Candida, Kluyveromyces, Yarrowia* or *Wickerhamomyces*. More preferably, the yeasts are selected from among *Saccharomyces cerevisiae, Pichia jadinii* (also called *Candida utilis*), *Pichia pastoris, Kluyveromyces lactis, Kluyveromyces marxianus, Yarrowia lipolytica, Wickerhamomyces anomalus* etc. These yeasts comprise between 6 and 11% of nitrogen. Nitrogen is measured with the Kjeldahl method known to skilled persons. As indicated above, the true protein content is extrapolated from this nitrogen assay using the multiplier coefficient 6.25.

The culture of yeasts is carried out following methods known to skilled persons. One protocol is described in the reference work «Yeast technology» by Gerald Reed and Tilak W. Nagodawithana (ISBN 0-442-31892-8) on pages 284 to 293. Said culture, also called biomass, is harvested by centrifugation or filtration and can be washed. A yeast cream is obtained.

The cells are then subjected to mechanical or chemical rupture using known methods such as high-pressure homogenization, mechanical grinding, ultrasound disintegration, repeated freeze-thaw cycles, osmotic shock or enzymatic lysis. In one preferred embodiment of the invention, the yeasts are subjected to thermal plasmolysis at a temperature of between 70 and 95° C. adapted according to yeast type. The temperature is preferably between 80 and 90° C. It is within the reach of those skilled in the art to adjust temperature and/or lysis time e.g. as a function of the resistance of the cells and/or enzymes it is desired to inactivate at this step. The time is between 30 seconds and 3 hours, up to 4 hours, more preferably 1 min., 5 min., 10 min., 30 min., 45 min., 1 h, 1 h30, or 2 h, up to 3 h, even 4 h. This plasmolysis step allows denaturing of the yeast, inactivation of endogenous enzymes and permeabilization of the membrane allowing release of a soluble fraction. The soluble fraction essentially comprises free amino acids, small peptides, minerals and among these amino acids some which have an impact on taste such as glutamic acid.

In a first embodiment of the invention, the whole derived from the plasmolysis step and containing the soluble fraction and insoluble fraction is subjected to one or more enzymatic activities. The objective of this step is to solubilise the maximum number of constituents that are not proteins, without attacking the proteins. Preferably ribonuclease activity (EC 3.1.4.1) and glucanase activity (EC 3.2.1) are used. The enzymatic activities can be implemented sequentially or simultaneously. Ribonuclease activity will convert RNA to 5' nucleotides and solubilise the latter causing it to move into the soluble fraction. It is possible to use several ribonucleases, and for example a mixture of endo- and exo-nucleases. Optionally, a deaminase can be used to convert AMP to IMP with a view to recovering the taste-enhancing property of the soluble fraction. The action of one or more glucanases will allow wall polysaccharides to be solubilised to soluble oligosaccharides. Time and temperature are to be adjusted as a function of the specifications of the enzymes used. The temperature is between 40 and 65° C., preferably 60° C. Time is between 8 and 24 hours, preferably between 16 and 24 h, more preferably 18 h. This enzymatic step first allows a novel soluble fraction to be obtained comprising nucleotides, polysaccharides (about 60% of total carbohydrates) and a small proportion of amino acids, and secondly an insoluble fraction essentially comprising the proteins.

The last step is a separation of the soluble fraction and insoluble fraction.

In a second embodiment of the invention, the soluble and insoluble fractions derived from the plasmolysis step are separated. The soluble fraction is set aside, removed and can be recovered as yeast extract. The insoluble fraction comprises the shells (or walls), polymers, polysaccharides, RNA, and the proteins coagulated by heat. This insoluble fraction is kept. It is subjected to the enzymatic activities of ribonuclease and glucanase such as indicated above, following a similar incubation protocol (temperature, time), and to separation of the soluble and insoluble fractions.

The final soluble fraction can be set aside and used.

The final insoluble fraction, derived from enzymatic digestion, has a content of «true» proteins higher than or equal to 70%, preferably higher than or equal to 72%, 80% and up to 85%. In general, the yeast comprises between 50 and 55% of «true» proteins. With the method of the invention, it is possible to remove many elements and to obtain a product with higher protein concentration. Optionally, the amount of lipids in this insoluble fraction can be reduced either via the action of solvents (ethanol, hexane) or via supercritical CO2 or through the action of a lipase or phospholipase. True protein purities of more than 80% can then be achieved.

In one embodiment of the invention, the respective actions of the ribonucleases and glucanases are implemented sequentially in any order. In one preferred embodiment of the invention, the ribonuclease and glucanase activities are applied at the same time.

The product obtained can be freeze-dried, dried with a method known to skilled persons, for example by spray drying or vacuum drying, and stored whilst maintaining its quality and properties.

Therefore, in one embodiment, the invention concerns a method for obtaining yeast proteins, comprising the following steps:
a) providing a yeast cream;
b) exposing this yeast cream to thermal plasmolysis at a temperature of between 70 and 95° C., for a time of between 1 minute and 3 hours, preferably between 40 minutes and 2 hours;
c) subjecting the whole to the activity of at least one ribonuclease and one glucanase, sequentially or simultaneously, at a temperature of between 40 and 65° C. for a time of between 8 and 24 hours;
d) separating the insoluble fraction and soluble fraction, wherein the insoluble fraction collected at step d) is taste-free, has a nucleotide content of less than 3% and true protein content of at least 72%.

In another embodiment, the invention concerns a method for obtaining yeast proteins, comprising the following steps:
a) providing a yeast cream;
b) exposing this yeast cream to thermal plasmolysis at a temperature of between 70 and 95° C., for a time of between 1 minute and 3 hours, preferably between 40 minutes and two hours;
b') separating the insoluble fraction and soluble fraction;
c) subjecting the insoluble fraction to the activity of at least one ribonuclease and one glucanase, sequentially or simultaneously, at a temperature of between 40 and 65° C. for a time of between 8 and 24 hours;
d) separating the insoluble fraction from the soluble fraction,
wherein the insoluble fraction collected at step d) is taste-free, has a nucleotide content of less than 3% and true protein content of at least 72%.

In the remainder of the present description, the insoluble fraction collected at step d) can also be called «(yeast) protein extract of the invention». On the contrary, a yeast protein extract obtained according to a known prior art method, from the soluble fraction derived from plasmolysis, can be called «conventional protein extract».

In one preferred embodiment of the invention, the yeast cream at step a) is derived from the fermentation of yeasts selected from among *Saccharomyces cerevisiae*, *Pichia* preferably *Pichia jadinii*, *Kluyveromyces* preferably *Kluyveromyces marxianus* or *Kluyveromyces lactis*, *Yarrowia* preferably *Yarrowia lipolytica*, or *Wickerhamomyces* preferably *Wickerhamomyces anomalus*. Advantageously, the yeast is selected from among *Saccharomyces cerevisiae*, *Pichia jadinii* or *Kluyveromyces marxianus*. The preferred yeast is *Saccharomyces cerevisiae*.

In one preferred embodiment of the invention, the thermal plasmolysis step a) is conducted at a temperature of between 80 and 90° C.

In one preferred embodiment of the invention, the glucanase and ribonuclease activities are applied simultaneously.

Optionally, deaminase activity can also be applied.

Advantageously, the yeast cream used at step a) contains a selenium-enriched yeast. Culture of selenium-enriched yeast can be carried out following a method known to skilled persons, for example the method described in application EP 1478732. The selenium content in the yeast culture can then reach 3 000 ppm or even higher.

The product obtained in the insoluble fraction has an exclusively proteinic nitrogen content higher than or equal to 11.5 dry matter %, i.e. 72% of true proteins (using the conversion coefficient of 6.25 given above). Normally, yeast has a maximum nitrogen content of 11%, which gives 69% potential proteins. Yeast also contains non-proteinic nitrogen material (nucleic acids, RNA, DNA). When subtracting nucleic nitrogen from total nitrogen, yeast only contains 50 to 55% of proteins. Therefore, the minimum content of 72% proteins obtained in the final insoluble fraction is characteristic of the method of the invention. In this same insoluble fraction, the total nucleotide content is between 0.8 and 1.5% and up to 3%, the total carbohydrate content is 1 to 8% (anthrone assay known to persons skilled in the art), with respective contents 0.2 to 4% for glucans, 0.2 to 4% for mannans, 7 to 15% for lipids, 1 to 7% for mineral matter.

It would be of interest to distinguish between a yeast protein extract obtained with the method of the invention and a prior art extract, namely a protein extract obtained from the soluble fraction after cell lysis and concentration step, which would have a protein content of at least 72% and possibly a nucleotide content of less than 3%.

For this purpose, the total lipids were assayed on protein extracts derived from *Saccharomyces cerevisiae*, using a gravimetric method after acid hydrolysis and extraction with hexane on Soxhlet apparatus. The lipid levels were systematically higher than 7%. Therefore, the insoluble fraction collected at step d) in an extraction method of the invention also has a lipid content higher than 7%. In comparison, the lipid content is lower than 1% in a «conventional» yeast protein extract. Lipid content can differ according to yeast species or strain. In general, for an industrial product, the starting microorganism is indicated in the technical datasheet. Persons skilled in the art will be able to extrapolate and infer a species/lipid content combination in the protein extract.

For a yeast protein extract of the invention subjected to a delipidation step, the lipid content may not be sufficient to distinguish between the two origins. An evaluation of the protein solubility profile of the protein extract can then complete the comparative analysis. Solubility percentage is determined with the following equation:

$$\% \text{ solubility} = \frac{\text{total N \% in the supernatant}}{\text{initial N \% in the reaction medium}}$$

where N % designates the nitrogen percentage, determined according to the Kjeldahl method.

The solubility of a protein extract of the invention is less than 3.5% in water.

In comparison, a «conventional» yeast protein extract is considered to be soluble, and only comprises between 5 and 10% of insoluble elements.

For the same purpose, the molecular weight profiles were compared between a yeast protein extract of the invention and a prior art protein extract. A yeast protein extract obtained with the invention does not exhibit a low molecular weight peak. Most of the protein profile is distributed around 40-45 kDa. The smallest compounds are found at about 500 Da, corresponding to small peptides. In comparison, the profile of a «conventional» yeast protein shows several molecular weight peaks and a non-negligible amount for low molecular weights. It is possible to extrapolate these profiles and to measure the ratio:

$$\frac{\text{total amino acids} - \text{free amino acids}}{\text{total amino acids}}$$

(amino acids assayed with a conventional assay method for amino acids in foods e.g. the official method of Commission Regulation (EC) No 152/2009). This ratio is close to 1, always higher than 0.9 for a yeast protein extract of the invention, whereas it can be between 0.30 and 0.85 for «conventional» yeast protein extracts.

The product obtained with the method of the invention sets itself apart from known protein extracts through its microbial origin, in other words non-plant and non-animal, its high protein content, low nucleic acid content, and remaining presence of cell membrane lipids if no delipidating treatment is applied. Additionally, it is taste-free. The microbial origin thereof also has the advantage that it is derived from a raw material which is not known to be allergenic.

Yeast proteins have the major advantage of their nutritional quality. Therefore, the product obtained with the method of the invention is a source of proteins which has one major advantage: its quality, represented by a PDCAAS score (Protein Digestibility Corrected Amino Acids Score) of 1, that is to say similar to that of reference animal proteins such as casein and ovalbumin. Evaluation of protein quality makes it possible to determine its capacity to meet metabolic needs. As a result, any application related to nutrition and food or sport supplements can use a protein extract obtained with the method of the invention. The applications cited herein are not intended to be exhaustive.

Within the context of human nutrition, health and well-being, said protein extract can be used for weight control, as supplement for sportspersons or the elderly, as food supplement or in the form of a high-protein bar or beverage. For example, said protein extract can be used as a source of non-animal protein for Vegan-type diets e.g. in milk-shakes, burgers, nuggets, plant-based deli meats, ravioli fillings, meatballs, oat flakes, pasta flavouring preparations. Similarly, protein-rich bread or breadmaking products can use the protein extracts obtained with the method of the invention. As previously indicated, these protein extracts have the advantage that they do not impart taste, bitterness or off-notes, characteristic of some of today's plant-based or algae proteins. In human health, said protein extract can be used for infant nutrition or clinical nutrition i.e. oral or enteral nutrition to remedy nutritional imbalance. Advantageously, when the protein extract is obtained from a selenium-enriched yeast cream, it can be used as food supplement stimulating immunity and/or reinforcing the quality of skin, hair and/or nails.

Finally said protein extract can be used as protein supply in animal feed. Advantageously, when the protein extract is obtained from a selenium-enriched yeast cream, animals will have the benefit of a combined supply of proteins and selenium, said selenium being bioavailable since it is integrated in the proteins in the form of selenomethionine.

The invention therefore also relates to the use of a yeast protein extract having a true protein content of at least 72%, obtained according to any of the embodiments of the method of the invention, as food supplement for weight control, for the elderly or sportspersons, to the use of said protein extract as a source of non-animal proteins in beverages, breadmaking products or plant-based deli meats, to the use of said protein extract in oral or enteral clinical nutrition, or to the use of said protein extract for animal nutrition. In other words, in one embodiment, the invention concerns a food supplementing method for human nutrition and/or animal nutrition, comprising the steps of:

obtaining a yeast protein extract by implementing any of the embodiments of the method for obtaining yeast proteins according to the invention; and administering said protein extract respectively to a human individual as food supplement for weight control, for the elderly or for sportspersons, and/or to an animal as protein intake.

As previously mentioned, the final soluble fraction of the method of the invention can also be set aside and used. Being high in total carbohydrates it can be compared to a sweet juice. The total carbohydrate content is between 45 and 70%. These carbohydrates are in the form of glucans (25 to 40%) and mannans (25 to 35%), allowing use of this soluble fraction for immunostimulation, in particular for animal health. Depending on the type of glucanase used, free glucose can also be released. This soluble fraction is rich in total nucleotides, more specifically in 5'-GMP and 5'-IMP when AMP is converted to IMP by a deaminase. It can therefore be used as taste enhancer. When AMP is not converted to IMP, the product can be used to mask bitterness or off-notes, as disclosed in patent application FR1762074. The composition thereof also makes it a good growth substrate for various microorganisms, and in particular for bacteria.

The examples below can illustrate the present invention. They cannot be construed as limiting the scope of the invention.

EXAMPLES

Example 1: Preparation of a Concentrated Protein Extract (>75%) from *Saccharomyces cerevisiae*

Conduct fermentation of *Saccharomyces cerevisiae* under conditions allowing high nitrogen content of the yeast to be reached, about 10 dry matter % of nitrogen. Use centrifugal separation on the must of this fermentation to obtain a yeast cream at 16-18 dry matter % of yeast, and wash the cream.

In the laboratory, carry out thermal plasmolysis on 3 kg of this nitrogen-rich, washed cream: bring the temperature of the cream to a temperature selected between 70 and 95° C. using an exchanger then leave the 3 kg of cream to incubate in a beaker immersed in a hot-water bath. Leave the cream under agitation and maintain the temperature of the cream in the beaker for 2 h. Then lower the temperature of the reaction medium to 60° C. Transfer a fraction to a 500 mL Erlenmeyer flask. Immerse the Erlenmeyer in a hot-water bath having a temperature adjusted to 60° C. Add the following doses of enzymes: 0.2% (g per 100 g of cream) of a mix of two glucanases and 0.1% of a mix of endo and exo-ribonucleases. Leave to incubate 18 h under agitation. Centrifuge after incubation. Set aside the soluble fraction containing free nucleotides, polysaccharides and a small proportion of amino acids. The insoluble fraction is the yeast protein extract. After 3 washings, the composition thereof is the following: 13.0% nitrogen, 3% total nucleotides and 4.7% total carbohydrates, i.e. 77% true proteins.

Example 2: Preparation of a Concentrated Protein Extract (75%) from Saccharomyces cerevisiae According to a Variant of Method 1

In a variant of the method described in Example 1, after thermal plasmolysis separate the insoluble fraction from the supernatant comprising the free amino acids by centrifugation. The insoluble fraction is taken up in a volume of mains water equivalent to the volume of discarded supernatant and again centrifuged. This operation is conducted a total of 3 times. Finally recover 2 kg of insoluble fraction at 16 dry matter % containing the proteins, polysaccharides and nucleic material. Transfer a fraction to a 500 mL Erlenmeyer. Immerse the Erlenmeyer in a hot-water bath having a temperature adjusted to 60° C. and apply thereto the remainder of the method such as described in the preceding example.

The composition of the protein extract finally obtained is the following: 12.2% nitrogen, 1.4% total nucleotides and 2.9% total carbohydrates, i.e. 75% true proteins.

Example 3: Preparation of a Concentrated Protein Extract (>80%) from Saccharomyces cerevisiae With the steps of thermal plasmolysis, centrifugal separation and washing, prepare the insoluble fraction of Saccharomyces cerevisiae containing proteins, polysaccharides and nucleic material following the protocol described in Example 2.

Adjust the dry extract of this fraction to 14% and pH to the optimum pH of the enzymes. Incubate 200 g of this fraction under agitation in an Erlenmeyer immersed in a hot-water bath at 60° C. for 18 h in the presence of the following enzymes doses: 0.2% of a purified liquid preparation of glucanase and 0.1% of a mix of endo and exo-ribonucleases. Collect the insoluble fraction by centrifugation and wash 3 times. The protein extract obtained comprises 13.6% nitrogen, 2.4% total nucleotides and 4.2% total carbohydrates i.e. 83% true proteins.

Example 4: Rapid Preparation of a Concentrated Protein Extract (75%) from Saccharomyces cerevisiae In one variant of the method described in Example 2, the incubation time can be reduced to 8 h. The protein extract obtained then comprises 12.5% nitrogen, 3% total nucleotides and 4.4% total carbohydrates, i.e. 75% true proteins.

Example 5: Preparation of a Concentrated Protein Extract (80%) from Saccharomyces cerevisae In one variant of the method described in Example 2, the protein extract is dried before extraction with five volumes of ethanol, washed, drained and again dried in vacuo. The protein extract obtained then comprises 13.3% nitrogen, 2% total nucleotides and 3.1% total carbohydrates, i.e. 81% true proteins.

Example 6: Preparation of a Concentrated Protein Extract from Pichia jadinii

Conduct fermentation of Pichia jadinii under conditions allowing a nitrogen content of the yeast to be obtained in the region of 9 dry matter %. Apply centrifugal separation to the must of this fermentation to obtain a yeast cream of 11-13 dry matter % and wash the cream.

In the laboratory, perform thermal plasmolysis on 3 kg of this nitrogen-rich cream at a temperature of between 70 and 95° C., for 2 h following the same protocol as applied to the strain Saccharomyces cerevisiae. Collect the insoluble fraction by centrifugation and wash 3 times.

Adjust the dry extract of this fraction to 11-13% and pH to the optimum pH of the enzymes. Incubate 200 g of this fraction under agitation in an Erlenmeyer immersed in a hot-water bath at 60° C. for 18 h in the presence of the following enzyme doses: 0.2% of a purified liquid preparation of glucanase and 0.1% of a mix of endo and exo-ribonucleases. Collect the insoluble fraction by centrifugation and wash 3 times. The protein extract obtained then comprises 11.7% nitrogen, 1.4% total nucleotides and 13.3% total carbohydrates, i.e. 72% true proteins.

Example 7: Preparation of a Concentrated Protein Extract from Kluyveromyces marxianus Conduct fermentation of Kluyveromyces marxianus under conditions allowing a nitrogen content of the yeast to be reached in the region of 8 dry matter %. Apply centrifugal separation to the must of this fermentation to obtain a yeast cream and wash the cream. Apply thermal plasmolysis, centrifuge, wash the insoluble fraction and incubate with a mix of enzymes containing glucans and endo and exoribonucleases following the protocol previously described. Centrifuge a further time and wash the insoluble fraction containing the proteins.

The protein extract obtained comprises 11.8% nitrogen, 1.3% total nucleotides and 8.8% total carbohydrates, i.e. 72% true proteins.

Example 8: Assay of Total Lipids in an «Insoluble» Protein Extract Obtained with a Method of the Invention and Comparison with the Lipid Content of a «Conventional» Yeast Protein Extract Extracted from the Soluble Portion of Yeasts after Cell Lysis According to the Prior Art The method used is a gravimetric method after acid hydrolysis and extraction with hexane on Soxhlet. apparatus. This method is described in EC regulation No. 152/2009. The results are given in Table 1 below. From three batches of protein extract obtained according to the invention, these results indicate a lipid content close to 10 to 11 g per 100 g of extract. In comparison, a yeast protein extract of the prior art, obtained from the soluble fraction of lysed yeasts, shows a lipid content of less than 1 g per 100 g of extract.

|  | Protein extract of the invention (from insoluble fraction) | | | Prior art protein extract (from soluble fraction) |
| --- | --- | --- | --- | --- |
|  | Batch 1 | Batch 2 | Batch 3 |  |
| Total lipids (g/100 g) | 11.2 | 10.8 | 11.1 | <1 |

Example 9: Determination of Protein Solubility Profile

On a sample derived from Batch 1 of protein extract according to the invention (cf. Example 8), the protein solubility profile was determined at three different pH values in aqueous solution and using a final protein concentration of 2% (w/v). After a solubilisation time of 60 minutes under agitation at ambient temperature, the supernatant was collected by centrifugation and the total nitrogen content in the supernatant was determined with the Kjeldahl method in accordance with standard NF EN ISO 5983-2. For each pH value, the solubility percentage was determined with the following equation:

$$\% \text{ solubility} = \frac{\text{total N \% total in the supernatant}}{\text{initial N \% in the reaction medium}}$$

The result obtained was lower than 3.5%.

Example 10: Determination of the Respective Molecular Weight Profiles of a Protein Extract of the Invention and a «Conventional» Protein Extract As in all the foregoing, «protein extract of the invention» designates a yeast protein extract obtained from the insoluble fraction of lysed yeast cells. On the contrary, a «'conventional' yeast protein extract» designates yeast proteins obtained by extraction from the soluble fraction of lysed yeast cells. Extraction performed with methods known to persons skilled in the art.

Figure 2:
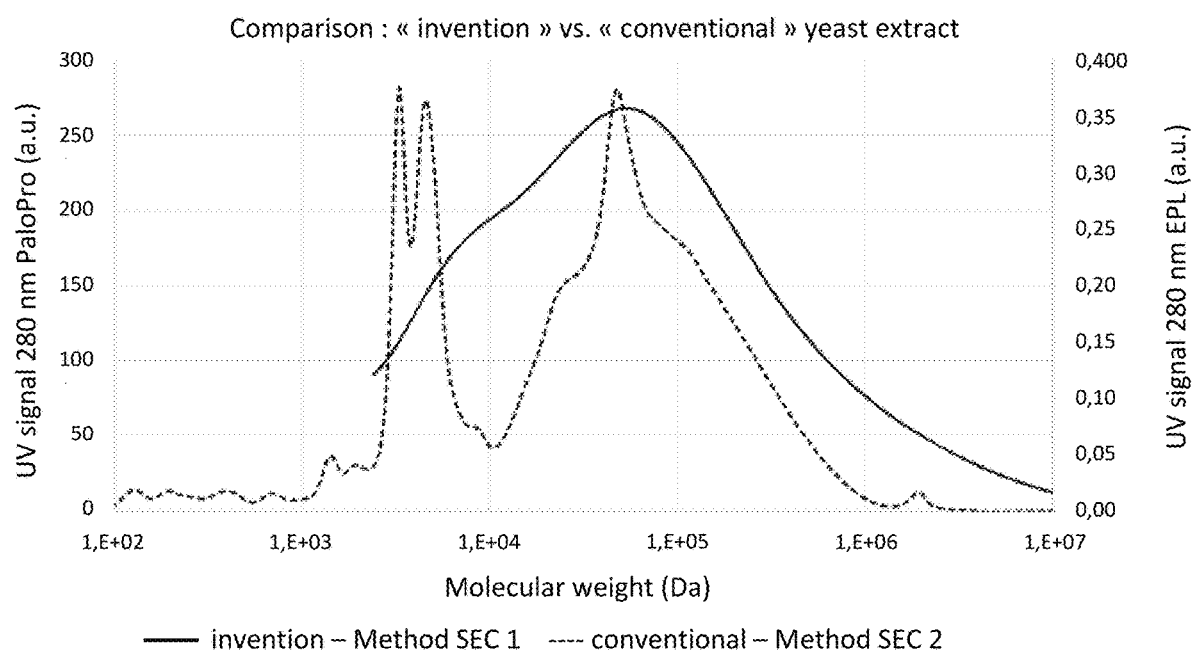
FIG. 2 gives the respective protein profiles of a protein extract derived from a method of the invention, and of a so-called conventional protein extract derived from a known method for extracting proteins from the soluble fraction obtained the plasmolysis step.

As indicated in Example 9, the protein extract of the invention is not soluble in aqueous conditions. Specific conditions for solubilisation and analysis by size exclusion chromatography have been developed. The protocol is the following (method SEC1 in FIG. 2):
solubilisation of 10 mg of sample in 5 mL of mobile phase (under agitation for 48 h at 90° C.),
analysis of the solution obtained on Agilent® PL gel column, 20 µm MIXED-A (2 000 to 40 000 000 g/mol, PS equivalent) at 40° C.
Mobile phase: DMSO/LiCl 0.25 M.
RI (refractive index) and UV (280 nm) detectors.
The method (method SEC2 in FIG. 2) used for the «conventional» yeast protein extract was taken from the OIV monograph (International Organisation of Vine and Wine):
solubilisation of the sample in water;
analysis on SUPERDEX 200 10/300 GL column (10 000 to 600 000 Da, globular protein equivalent; 1 000 to 100 000 g/mol, dextran equivalent).
Mobile phase: phosphate buffer+0.25 M NaCl, pH 7.2
UV Detection at 214, 260 and 280 nm.
The respective protein profiles are given in FIG. 2.
The protein extract profile of the yeast of the invention is distributed around 45 kDa and does not exhibit a peak of low molecular weight (range 2-10 kDa). In comparison, the protein extract profile of a «conventional» yeast differs significantly: it exhibits two distinct peaks in the range of low molecular weights, 2-10 kDa, and overall a profile with peaks that are more distinct and more outspread.

Assay of total amino acids and free amino acids in accordance with the official method given in EU EC Regulation No. 152/2009 also allows determination of the ratio:

$$\frac{\text{total amino acids} - \text{free amino acids}}{\text{total amino acids}}$$

This is very close to 1 (or 100%) and always higher than 0.9 (or 90%) on a yeast protein extract of the invention (determination on the 3 batches for which lipids were assayed in Example 8). It is conventionally between 0.30 and 0.85 (30 to 85%) for «conventional» yeast protein extracts of the Applicant, and commercially available extracts.

Example 11: Preparation of a Concentrated Protein Extract (>75%) from a Culture of Selenium-Enriched *Saccharomyces cerevisiae*

A batch of selenium-enriched yeast cream was subjected to the protein extraction method described in Example 1 or Example 2. The selenium content in this yeast cream was close to 3 200 ppm.
The total nitrogen content in the protein extract obtained was 13.5%, the true protein content was 76.7%. Total selenium content was 4 750 ppm (mg Se/kg, dry). The selenomethionine content was 84% (Eq. Se/Se tot). In comparison, the selenized yeast SelSaf®3000, source of bioavailable organic selenium, has a 63% content of selenomethionine.

The invention claimed is:
1. A method for obtaining yeast proteins, comprising the following steps:
   a) providing a yeast cream;
   b) exposing this yeast cream to thermal plasmolysis at a temperature of between 70 and 95° C. for a time of between 30 seconds and 4 hours;
   c) subjecting the whole to the activity of at least one ribonuclease and one glucanase, sequentially or simultaneously, at a temperature of between 40 and 65° C. for a time of between 8 and 24 h;
   d) separating the insoluble fraction and soluble fraction;
   wherein the insoluble fraction collected at step d) is taste-free, has a nucleotide content of less than 3% and true protein content of at least 72%.
2. The use of a yeast protein extract having a true protein content of at least 72%, obtained with the method of claim 1, in human nutrition or in animal nutrition comprising feeding the yeast protein extracts to a human or animal.
3. The use of claim 2, wherein the yeast protein extract is used as a food supplement for weight control, for the elderly, or for sportspersons, comprising supplementing a diet with the yeast protein extract for weight control, for the elderly, or for sportspersons.
4. The method of claim 1, wherein deaminase activity is also applied at step c).
5. The method of claim 1, wherein the yeasts are selected from the group consisting of the species *Saccharomyces, Pichia, Candida, Kluyveromyces, Yarrowia* and *Wickerhamomyces*.

6. The method of claim 1, wherein the yeasts are selected from the group consisting of *Saccharomyces cerevisiae, Pichia jadinii* and *Kluyveromyces marxianus*.

7. The method of claim 1, wherein the enzymes used at step c) are used simultaneously.

8. The method of claim 1, wherein the insoluble fraction collected at step d) also has a lipid content higher than 7%.

9. The method of claim 1, wherein the insoluble fraction collected at step d) is treated with ethanol, a solvent or supercritical $CO_2$ to remove the lipids and increase the true protein content to 80%.

10. The method of claim 1, wherein the yeast cream used at step a) contains a selenium-enriched yeast.

\* \* \* \* \*